United States Patent [19]

Craig

[11] 4,057,350
[45] Nov. 8, 1977

[54] APPARATUS FOR COUNTING CRIMP IN FIBERS

[75] Inventor: Jeffrey M. Craig, Princeton, N.J.

[73] Assignee: Akzona Incorporated, Asheville, N.C.

[21] Appl. No.: 717,736

[22] Filed: Aug. 24, 1976

[51] Int. Cl.² .............................................. G01N 23/20
[52] U.S. Cl. ..................................... 356/199; 73/160; 250/571; 356/238
[58] Field of Search ............... 356/119, 200, 238, 242; 250/559, 571; 73/160

[56] References Cited

U.S. PATENT DOCUMENTS

| 2,427,753 | 9/1947 | Vose et al. ........................ 250/562 |
| 3,193,688 | 7/1965 | Morton et al. ..................... 356/238 |
| 3,985,451 | 10/1976 | Plockl ............................. 356/199 |

Primary Examiner—John K. Corbin
Assistant Examiner—Richard A. Rosenberger
Attorney, Agent, or Firm—Tom R. Vestal; Francis W. Young

[57] ABSTRACT

An apparatus is provided for counting crimp in fibers or filaments by moving a cell containing a specimen through a laser beam and detecting changes in radiation scattered by the crimped fiber. The radiation is observed by means of suitable electronic circuitry and a photodetector.

10 Claims, 13 Drawing Figures

A, C, E, G, I
(NO PATTERN)

A, C, E, G, I
(NO PATTERN)

B, F

B, F

D, H

D, H

APPARATUS FOR COUNTING CRIMP IN FIBERS

BACKGROUND OF THE INVENTION

The trend in modern fiber technology is toward the production of artificial yarns as uniform continuous filaments which are stronger than spun yarns. However, continuous filaments have a disadvantage for a number of applications; for example, in clothing, they lack bulk and have insufficient covering power. It is for this reason that processes for crimping or texturing continuous filaments, e.g., falsetwist texturing, the knit-deknit process, edge crimping, air jet treating, stuffer box bulking and chemical and/or thermal treatment, have been so extensively developed. Crimp is also introduced into rayon fibers by controlling the process of manufacture, for example, by adjusting the composition of the regenerating acid bath.

Therefore, in the manufacture of many types of textile yarns and fibers, the amount of crimp in a unit length of filament or fiber is of great importance and the measurement of crimp is a quality control test which is frequently used.

The usual procedure for counting the crimp in a filament or fiber is to place a representative sample alongside a length scale on a black velvet-covered board and then, with the aid of a magnifying glass, visually count the half-waves of crimp in a unit of scale length. The crimp count per unit length is normally considered one-half the count so obtained.

Disadvantages of the above method are the use of the human eye for very fine tedious work, as the crimp diameter may typically be only about 0.5 mm. to 1.5 mm., and rather poor reproducibility.

SUMMARY OF THE INVENTION

This invention comprises an apparatus for counting crimp in filamentary material such as fibers or filaments, particularly of textile fibers or filaments. The apparatus preferably counts one complete wave in the crimp as one unit.

The invention utilizes a laser beam for counting the number of crimps in a unit length of a fiber. The fiber, mounted between transparent plates, is drawn lengthwise transversely through the beam. Scattered light pulses caused by fiber crimps are separated from the central beam and transmitted to a photodetector by positioning of a fiber optics conduit or by use of a baffle and lenses. By means of suitable electronic circuits, the output of the photodetector is converted into signals to operate a counting device which counts the number of crimps.

BRIEF DESCRIPTION OF THE DRAWINGS

The invention will now be further described with reference to the appended drawings, in which.

DESCRIPTION OF THE PREFERRED EMBODIMENTS

Figure 1:
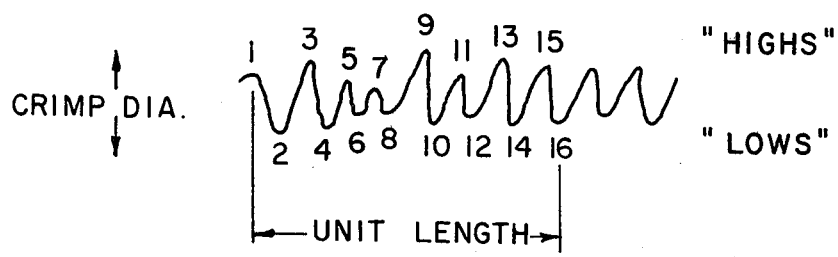
FIG. 1 illustrates a visual method of counting crimp in a fiber.

In FIG. 1, a representation of a fiber is shown greatly magnified. Conventionally, the crimp of the yarn is determined by mounting the fiber on a velvet-covered board of contrasting color having a unit scale positioned thereon. The magnitude of the crimps is shown as "crimp diameter." Through a magnifying glass, half wavelengths are counted with a teaser or pick by alternating between high nodes 1, 3, 5, 7, 9, 11, 13, and 15 and low nodes 2, 4, 6, 8, 10, 12, 14, and 16 of the crimped yarn. The result obtained is then divided by two. For example:

(16 crimp nodes/unit length)/2 = 8 crimps/unit length

The latter is commonly called the "crimp count" of the fiber.

Figure 2:
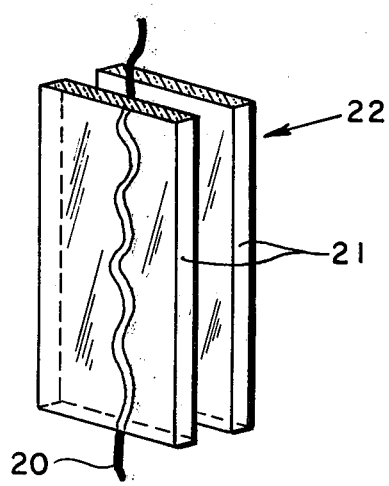
FIG. 2 is a perspective drawing of the method of mounting a fiber sample in a specimen cell.
Figure 3:
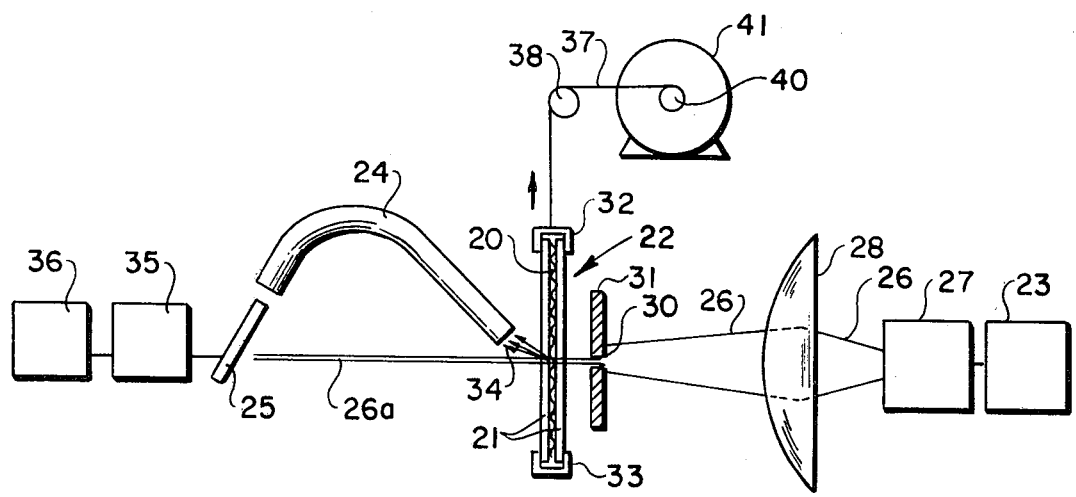
FIG. 3 is a cross-sectional diagram showing one embodiment of the invention in which a fiber optics conduit is used.
Figure 4:
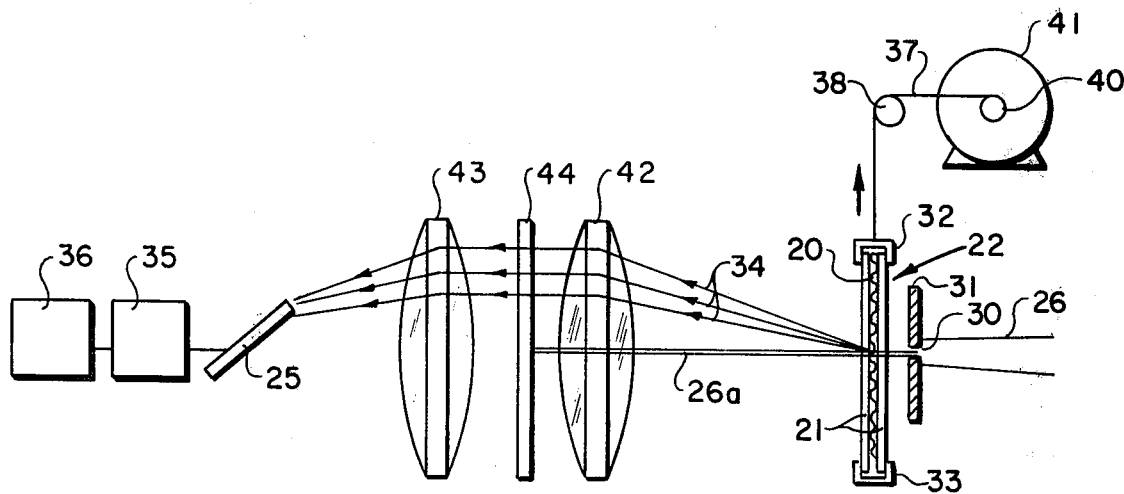
FIG. 4 is a cross-sectional diagram of a second embodiment of the invention in which lenses are used instead of a fiber optics conduit.

In FIG. 2, an exploded, perspective drawing illustrates in the present invention how the fiber 20 may be mounted between two transparent plates 21 of a specimen cell 22 for utilization in the embodiments shown in FIG. 3 and FIG. 4.

In FIG. 3, a diagram of one embodiment of the invention shows one arrangement of the laser 23, specimen cell 22, fiber optics conduit 24, and photodetector 25. The laser beam 26 may pass through the spatial filter 27 and be focused by a cylindrical lens 28. It is also possible to focus the laser beam 26 directly without use of the spatial filter 27 and the cylindrical lens 28. A section of the beam passes through the horizontal slit 30 in the plate 31. The slit may have a height, for example, of 0.04 millimeters, forming a relatively wide, thin beam 26a which passes through the area occupied by the fiber sample 20 held in the specimen cell 22. The plates 21 of the specimen cell 22 are held together by clamps 32 and 33. The specimen cell 22 is moved at a steady rate in a direction lengthwise of the fiber 20 shown by the arrow, causing a varying scattered radiation pattern 34 to be generated by the laser beam 26a striking the fiber 20. As will be described hereinafter in more detail (see FIGS. 5 through 8), the end of the fiber optics conduit 24 is positioned, for example, in a quadrant above half of the beam, so only a portion of the scattered radiation 34 strikes one end of the fiber optics conduit 24 and is transmitted to the photodetector 25 which is adjacent the other end of the conduit. As the laser beam 26a passes along crimps in the fiber 20, the radiation will stimulate the photodetector 25 in intermittent pulses. The output of the photodetector 25 is converted by means of electronic circuitry 35 (shown in FIG. 13) to operate a counter 36, which counts the number of crimps.

Specimen cell 22 may be moved, for example, by a framework constructed with a vertical track through which the specimen cell 22 slides. The specimen cell 22 may be raised by means of a cord 37 which is attached to the specimen cell 22 and which passes over a pulley 38 and is wound on the shaft 40 of a low rpm synchronous motor 41.

In FIG. 4, a second embodiment of the invention is shown in which a different method of transmitting the scattered radiation pattern 34 to the photodetector 25 is used. As in FIG. 3, the laser beam 26 passes through a slit 30 in plate 31 and strikes the fiber sample 20 which is held in the specimen cell 22. The scattered radiation pattern 34 in this embodiment is focused on the photodetector 25 by means of double convex lenses 42 and 43 and a baffle 44 positioned between the lenses 42 and 43. The baffle 44 serves to prevent the intense central bright band of the laser 26a from striking the photodetector 25 and thus allows examination of the much less intense scattered radiation pattern 34, and also to eliminate other scattered radiation which would be counted as half wave lengths (see FIG. 5 and FIGS. 9 through 11).

In FIGS. 5 through 11, the scattering effect of the laser beam 26a striking various portions of the fiber 20 and the spatial relation of the resulting scattered radiation pattern to the end of the fiber optics conduit 24 (see FIG. 3) or the side of the baffle 44 (see FIG. 4) is illustrated.

The principle on which the invention depends is light scattering, rather than the minute changes in the intensity of the central bright beam 26a after the interposition of the fiber 20 in the beam 26a. The scattered radiation pattern 34 appears radially and at different angles as the position of the fiber 20 relative to the laser beam 26a changes. The pattern produced corresponds with the spatial orientation of the segment of the fiber 20 in the beam 26a.

Figure 5:
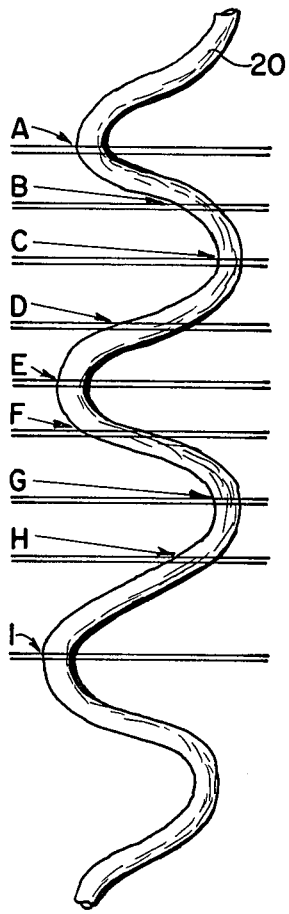
FIG. 5 is a representation of a laser beam striking different parts of a fiber.
Figure 6:
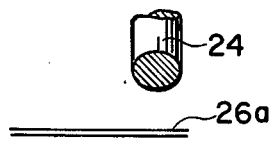
FIGS. 6, 7, and 8 illustrate the position of scattered light relative to the end of a fiber optics conduit in one embodiment of the invention.
Figure 9:
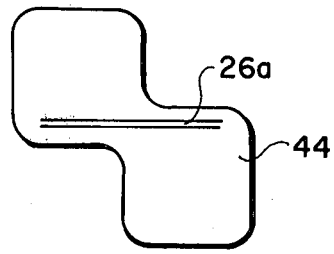
FIGS. 9, 10, and 11 illustrate the position of scattered light relative to a baffle in a second embodiment of the invention.
Figure 7:
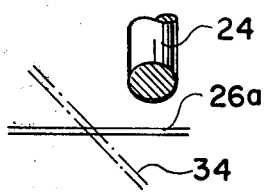
Figure 10:
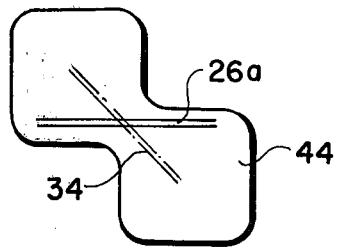
Figure 8:
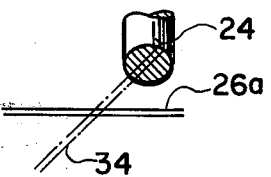
Figure 11:
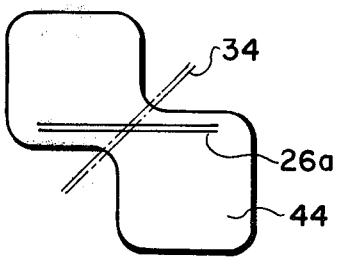

After passing through a slit 30 (as shown in FIGS. 3 and 4), the wide, thin laser beam 26a strikes the fiber 20 transversely as it is drawn in a lengthwise direction through the beam 26a. In FIG. 5, the laser beam 26a at successive positions in relation to the fiber 20 is represented by the lines A, B, C, D, E, F, G, H, and I. At position A, because the fiber 20 is perpendicular to the laser beam 26a, there is no scattered radiation pattern 34 to be conducted through the lenses 42 and 43 (see FIG. 4) or the fiber optics conduit 24 (see FIG. 3). At position B, a pattern forms but is prevented from being detected and counted by the positioning of the fiber optics conduit 24 in FIG. 3 and by use of a baffle 44 in FIG. 4. As the laser beam passes position C, again the fiber 20 is perpendicular to the laser beam 26a and no scattered radiation pattern is formed, but at position D the radiation pattern is formed and this time the light is conducted to the photodetector 25 by the fiber optics 24 in FIG. 3, or by focusing through lenses 42 and 43 in FIG. 4. The whole process is repeated as the beam 26a passes the points E, F, G, H, and I. Positions A, C, E, G, and I (no pattern) are illustrated by FIG. 6 and FIG. 9; positions B and F (scattered light not being transmitted) by FIG. 7 and FIG. 10; and position D and H (scattered light being transmitted) by FIG. 8 and FIG. 11. The result is an intermittent stimulation of the photocell corresponding to the number of whole "waves" or crimps in the fiber. Electronic circuits as later described cause the successive stimulations of the photodetector to be counted.

Figure 12:
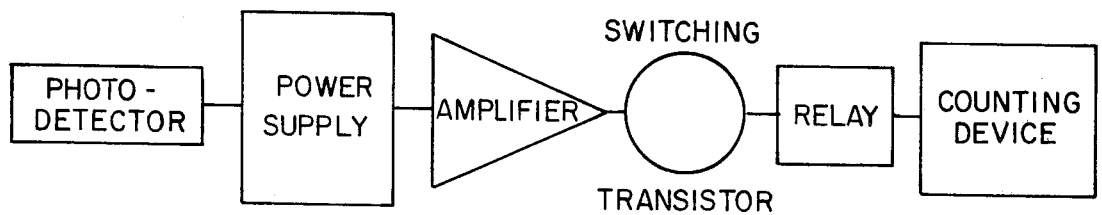
FIG. 12 is a block diagram of the apparatus and electronic circuitry used in the invention.

In FIG. 12, a block diagram of the electronic circuit for counting the pulses from the photodetector is shown. The photodetector output is conducted with the use of a power supply and operation amplifier through a switching transistor and relay to operate a counting device.

Figure 13:
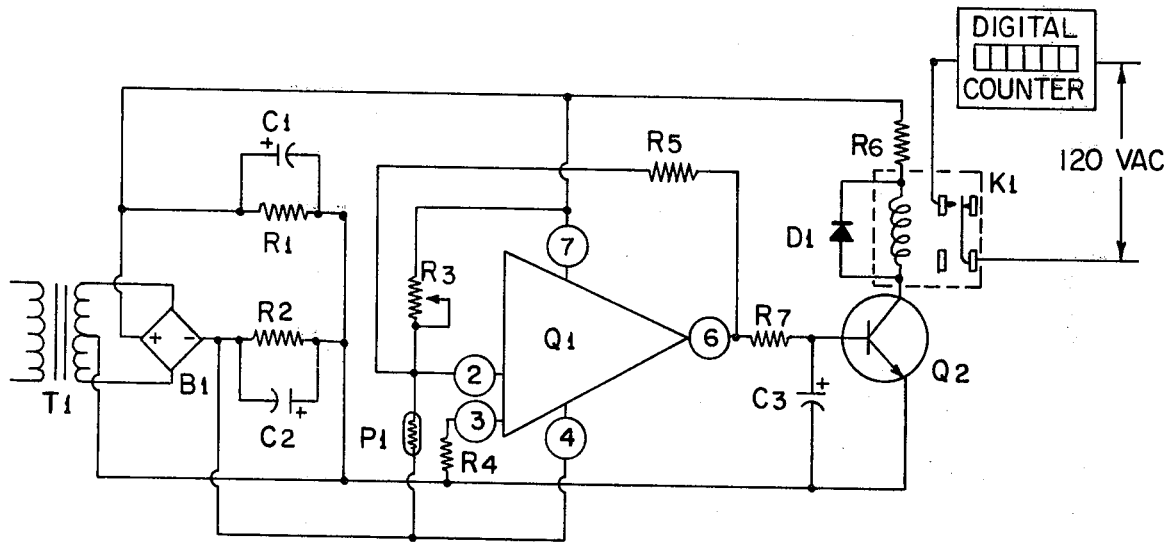
FIG. 13 is a detailed circuit diagram of the electronic circuitry shown in FIG. 12.

In FIG. 13, a circuit diagram is given of an electronic circuit for counting the pulses from the photodetector. The transformer T1, rectifier B1 and associated components constitute the power supply for the circuit. When the photodetector P1 is stimulated by a pulse of scattered light, its resistance is decreased, producing a negative voltage pulse at pin 2 of the operation amplifier $Q_1$. $Q_1$ is an inverting amplifier with a high gain. The positive output of $Q_1$ at pin 6 produces a momentary saturation voltage at the transistor $Q_2$, energizing the relay $K_1$ and causing the counter to count once.

A photocell, a photodiode, or a phototransistor may be used as the photodetector. Adjustments may be made using the potentiometer $R_3$ to compensate for differing characteristics of these devices.

The circuitry components of an embodiment utilizing a photocell detector are as follows:

Resistor $R_1$ — 6.8 K.
Resistor $R_2$ — 6.8 K.
Resistor $R_3$ — 0.5 megohms
Resistor $R_4$ — 1 K
Resistor $R_5$ — 20 megohms
Resistor $R_6$ — 100 K
Resistor $R_7$ — 10 K
Diode $D_1$ — IN34A
Op. Amp. $Q_1$ — 741C
Transistor $Q_2$ — 2N2222
Rectifier $B_1$ — Full wave bridge rectifier
Transformer $T_1$ — Primary 120 VAC 60 $H_2$: Secondary 25.2 VCT a 500 ma D.C.
Relay $K_1$ — 120 VDA SPDT 3 amp. relay
Capacitor $C_1$ — 100 F 50 VDC
Capacitor $C_2$ — 100 F 50 VDC
Capacitor $C_3$ — 15 F 25 VDC
Capacitor $V_1$ — 120 VAC 60 HZ The operating steps in making a determination of crimp count with the apparatus of this invention are as follows:

1. The optics of the system are aligned and the fiber optics 24 (as shown in FIG. 3) or lens 42 and 43 and baffle 44 (as shown in FIG. 4) are positioned.
2. The fiber 20 is mounted in the specimen cell 22.
3. The cell 22 is placed in the proper position to be moved through the laser beam 26.
4. The circuitry 35 (as described in FIG. 13) with the photodetector 25 is adjusted to respond to the scattered radiation pattern 34.
5. The counter 36 is turned to zero.
6. The cell 22 is drawn through the path of the laser beam 26a, causing the scattered radiation pattern 34 to strike the fiber optics 24 in one embodiment or lenses 42 and 43 in a second embodiment, in intermittent pulses, then travel to the photodetector 25 and activate the counter 36.
7. After the unit length of fiber 20 has passed through the laser beam 26a, the crimp count is recorded directly from the counter 36.
8. The counter 36 is reset for the next crimp count.

Other embodiments to the invention disclosed above may become apparent to those skilled in the art and the invention is not to be considered limited to the embodiments so described but shall be as set forth in the following claims.

What is claimed is:

1. An apparatus for counting crimps in a unit length of a fiber, comprising means for generating a laser beam, a plate having a slit through which the laser beam is passed, a cell to hold the fiber in a fixed position, means for moving the cell transversely through the laser beam lengthwise of the fiber, means for conducting pulses from scattered radiation caused by crimps in the fiber being moved through the laser beam, means for converting pulses from scattered radiation to electrical pulses, and means for counting electrical pulses, whereby as the fiber is moved transversely through the laser beam, pulses from scattered radiation caused by fiber crimps are conducted to the converting means, converted to electrical pulses, and counted, thereby counting the crimps in the fiber.

2. The apparatus of claim 1 where the means for generating a laser beam is a helium-neon laser.

3. The apparatus of claim 1 where the means for moving the cell transversely through the laser beam comprises a cord which is attached to the cell and which passes over a pulley and is wound on the shaft of a motor.

4. The apparatus of claim 1 wherein the means for conducting scattered radiation pulses is a fiber optics conduit having one end positioned in a quadrant above a cross-section of half of the laser beam with the other end positioned adjacent the means for converting pulses from scattered radiation to electrical pulses.

5. The apparatus of claim 1 where the means for conducting pulses from scattered radiation comprises two convex lenses and a baffle positioned between the lenses.

6. The apparatus of claim 1 where the means for converting pulses from scattered radiation to electrical pulses comprises a photodetector and a means for converting output pulses from the photodetector to electrical pulses and amplifying the electrical pulses.

7. The apparatus of claim 6 where the photodetector is a photocell.

8. The apparatus of claim 6 where the photodetector is a photodiode.

9. The apparatus of claim 6 where the photodetector is a phototransistor.

10. The apparatus of claim 6 where the means for converting output pulses from the photodetector to electrical pulses is an electric circuit comprising a power supply, an operation amplifier, a switching transistor, and a relay.

* * * * *